United States Patent [19]
Tan

[11] Patent Number: 6,132,593
[45] Date of Patent: Oct. 17, 2000

[54] METHOD AND APPARATUS FOR MEASURING LOCALIZED CORROSION AND OTHER HETEROGENEOUS ELECTROCHEMICAL PROCESSES

[76] Inventor: Yong-Jun Tan, 15 Suelex Street, Willetton, Perth, Western Australia, Australia

[21] Appl. No.: 09/093,576

[22] Filed: Jun. 8, 1998

[51] Int. Cl.$^7$ .................................................. G01N 17/04
[52] U.S. Cl. .................................... 205/776.5; 205/775.5; 205/776; 205/777; 204/404; 324/71.1; 324/693; 324/700
[58] Field of Search ........................ 204/404; 205/775.5, 205/777, 776.5, 794.5, 776; 324/71.1, 71.2, 693, 700, 425, 348

[56] References Cited

U.S. PATENT DOCUMENTS

| | | |
|---|---|---|
| 4,575,678 | 3/1986 | Headky . |
| 5,139,627 | 8/1992 | Eden et al. . |
| 5,411,646 | 5/1995 | Gossett et al. ........................... 204/280 |
| 5,437,773 | 8/1995 | Glass et al. .............................. 204/404 |

OTHER PUBLICATIONS

Yong–Jun Tan, The Effect of Inhomogeneity in Organic Coatings on Electrochemical Measurement Using a Wire Beam Electrode, Part I, Progress in Organic Coatings, 1991, pp. 89–94, vol. 19, Elsevier Sequoia, Netherlands, No Month Available.

Yong–Jun Tan and Yu Shiti, The Effect of Inhomogeneity in Organic Coatings on Electrochemical Measurement Using a Wire Beam Electrode, Part II, Progress in Organic Coatings, 1991, pp. 257–263, vol. 19, Elsevier Sequoia (Publisher), Netherlands, No month available.

Yong–Jun Tan, A New Crevice Corrosion Testing Method and its Use in the Investigation of Oil Stain, Corrosion, 1994, pp. 266–269, vol. 50, NACE International, U.S.A, No month available.

Chi–Lan Wu, Xie–Jun Zhou and Yong–Jun Tan, A Study on the Electrochemical Inhomogeneity of Organic Coatings, Progress in Organic Coatings, 1995, pp. 379–389, vol. 25, Elsevier Science S.A., Switzerland, No month available.

Yong–Jun Tan, Wire Beam Electrode: A New Tool for Localised Corrosion Studies, Proceedings of Australasian Corrosion Association Corrosion & Prevention 97, Nov. 9–12, 1997, Paper No. 52, Australasian Corrosion Association (Publisher), Australia.

(List continued on next page.)

*Primary Examiner*—Bruce F. Bell

[57] ABSTRACT

An electrochemical method for measuring localized corrosion and other heterogeneous electrochemical processes is described. A multi-sensor electrode namely the wire beam electrode, integrated by coupling all its wire terminals together, is used to simulate a conventional one-piece metal electrode surface in electrochemical behavior. The working surface of the wire beam electrode is exposed to an electrolyte as a conventional one-piece electrode to allow heterogeneous electrochemical processes such as localized corrosion to occur. Electrochemical parameters at local areas of the wire beam electrode surface are detected by means of wires located at those areas. A zero resistance ammeter is inserted between each selected wire terminal and all other coupled wire terminals to measure the coupling current flowing into or out the selected wire, and thus a coupling current distribution map is produced. A high impedance voltmeter is used to measure the electrochemical potential of each temporarily uncoupled wire versus a reference electrode, and thus an electrochemical potential distribution map is produced. A polarization resistance measuring apparatus is used to measure the polarization resistance of each temporarily uncoupled wire, and thus a polarization resistance distribution map is produced. These electrochemical parameters and maps are used to determine the kinetics of heterogeneous electrochemical processes using equations described in this disclosure. This method and apparatus can be used to measure various forms of heterogeneous electrochemical processes such as localized corrosion, cathodic and anodic protection, electroplating, electro-machining, electrotyping and electrowinning.

5 Claims, 10 Drawing Sheets

OTHER PUBLICATIONS

Yong–Jun Tan, Monitoring Localized Corrosion Processes and Estimating Localized Corrosion Rates Using a Wire–Beam Electrode, Corrosion, 1998, pp. 403–413, vol. 54, NACE International, U.S.A., No month available.

Yong–Jun Tan and Yu Shiti, Study and Evaluation of Organic Coatings by Use of a Wire Beam Electrode; Proceedings 7$^{th}$ Asian and Pacific Corrosion Control Conference, Beijing, p. 671 (Cumulative Publication), No month/year available.

Yong–Jun Tan and Yu Shiti, Study and Evaluation of Organic Coatings by Use of a Wire Beam Electrode; Materials Protection (China), vol. 25, No. 6, pp. 6–23 (1992) (Cumulative Publication), No month available.

Wu C.L., Zhong, Q. D. and Jin, J.C. Study on Electrochemical Inhomogeneity on Oil–Painted Metal, Corrosion Science and Protection Technology (China), vol. 8, No. 3, p. 256 (1996) No month available.

Huang, G. F., Wu, C.L. and Jin, J.C. Study on Protective Behaviour of Rust Preventing Oil by Wire Beam Electrode; Materials Protection (China), vol. 29, No. 4, p. 9 (1996), No month available.

A schematic diagram illustrating the conceptual design of the wire beam electrode.

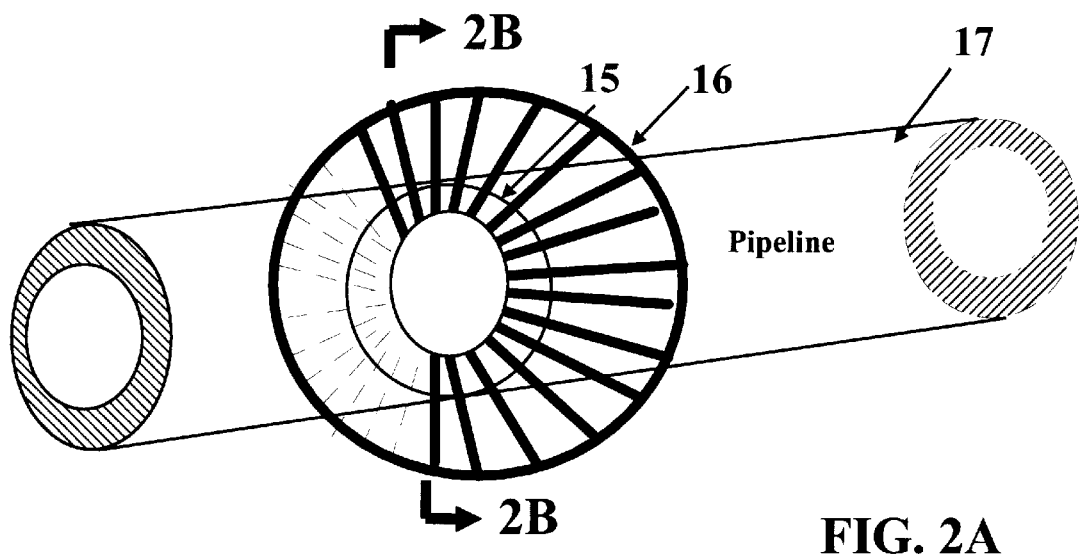
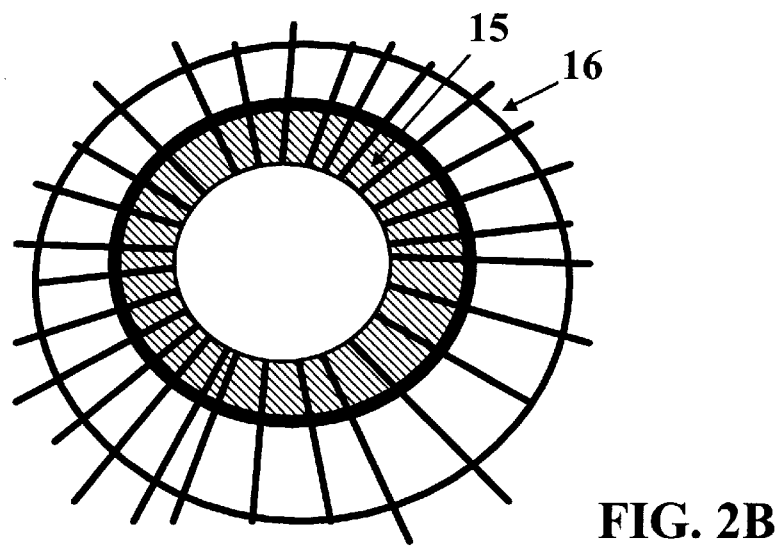
A schematic diagram illustrating a wire beam electrode with the configuration of a tube.

A schematic diagram illustrating a wire beam electrode with the configuration of a rod.

A schematic diagram illustrating galvanic current measurement of a wire beam electrode system exposed to a corrosive electrolyte.

A schematic diagram illustrating electrochemical potential measurement of a wire beam electrode system exposed to a corrosive electrolyte.

A schematic diagram illustrating electrochemical polarization measurement of a wire beam electrode system exposed to a corrosive electrolyte.

The distributions of galvanic current and corrosion potential measured from a wire beam electrode system exposed to a water-line corrosion environment.

A schematic diagram illustrating the measurement of cathodic protection current distribution over a wire beam electrode surface exposed to a concrete structure with sacrificial anodes present.

The measurement of cathodic protection current distribution over a wire beam electrode surface which is under impressed current cathodic protection.

The measurement of electroplating current distribution over a wire beam electrode surface.

METHOD AND APPARATUS FOR MEASURING LOCALIZED CORROSION AND OTHER HETEROGENEOUS ELECTROCHEMICAL PROCESSES

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The present invention relates principally to electrochemical measurement, and more specifically to the measurement of localized electrochemical corrosion and other heterogeneous electrochemical processes such as cathodic and anodic protection of metals, electroplating, electrotyping, electrometallurgy, electrowinning and electromachining.

2. Description of the Related Art

A metal surface exposed to an electrolyte is often electrochemically non-uniform due to factors such as a localized chemical environment over the metal surface, an inhomogeneous metallurgical structure in the metal surface, localized defects in a surface protective film which covers the metal surface, and a polarization voltage which non-uniformly polarizes the metal surface. This electrochemical non-uniformity is a common natural phenomenon and is referred to as electrochemical heterogeneity. Electrochemical processes occur over a heterogeneous metal surface are referred to as heterogeneous electrochemical processes. Heterogeneous electrochemical processes are characterized by a marked difference in electrochemical parameters, such as electrochemical potential, over the metal surface.

Heterogeneous electrochemical processes are very common in practice and often play a key role in corrosion and electrochemical industries. Localized corrosion such as pitting corrosion and crevice corrosion is probably the most common heterogeneous electrochemical process. Localized corrosion often causes premature, in some cases, catastrophic failure of industrial structures. When localized corrosion occurs, there is a spatial separation of the anodic and cathodic areas. Different electrochemical reactions occur on the anodic and cathodic areas and there is a marked potential difference between anodic and cathodic areas. This electrochemical potential difference drives galvanic current to flow between anodic and cathodic areas simultaneously in the metal and in solution, resulting in rapid localized corrosion penetration to occur at anodic areas. Heterogeneous electrochemical processes also play a key role in cathodic and anodic protection of metals, electroplating, electrotyping, electrometallurgy, electrowinning, electromachining. In the case of cathodic protection of a metal structure using a sacrificial anode, protection current (galvanic current) is not uniformly distributed over the metal structure surface. Locations that are far away from the sacrificial anode site often have low protection current density and thus may not be effectively protected. This is a major problem that has to be addressed when a cathodic protection system is designed. Similar problems arise when impressed cathodic protection current is applied to a metal structure such as a long pipeline with protective current density decaying as the distance to impressed current source increases. In this case, locations far away from the current source may not be effectively protected. Electrochemical heterogeneity is also a key factor for anodic protection. Indeed, anodic protection potential and its distribution is of major concern and it could significantly affect the efficiency and reliability of an anodic protection system. Electrochemical heterogeneity is also common in electroplating and electrotyping. If a work-piece (an electrode) has a complex shape, the distribution of electrochemical reaction current (electroplating or electrotyping current) can be very non-uniform over the surface of the work-piece and this electrochemical heterogeneity can influence the quality of electroplating and electrotyping. In the case of electrometallurgy and electrowinning, electrochemical heterogeneity can result in a non-uniform electrodeposition and can influence the structure of crystals. In an electromachining processes, electrochemical heterogeneity could also affect the precision of electromachining, especially when a work-piece has a complex shape.

The measurement of heterogeneous electrochemical processes is an important requirement for characterizing, monitoring, controlling and optimizing these industrially important processes. However, the measurement of heterogeneous electrochemical processes is a major difficulty in electrochemical and corrosion science and engineering. This is because conventional electrochemical techniques have major limitations in measuring local electrochemical parameters and in determining local electrochemical kinetics. It is well known that conventional electrochemical techniques use a one-piece metal electrode which only measures mixed and averaged electrochemical parameters over the whole electrode surface. When a one-piece electrode is used, it is impossible to measure the galvanic current that flows between localized anodic and cathodic sites in the electrode body since an ammeter is not able to be inserted between anodic and cathodic sites which are located on a single piece of metal surface. It is also well known that traditional electrochemical techniques have major difficulties in determining heterogeneous electrochemical kinetics. This is because traditional electrochemical kinetic theories are based on a one-piece electrode with an ideally uniform working surface. The fundamental formulation describing the electrochemical kinetics over the metal surface, the Butler-Volmer equation, is based on a uniform electrochemical corrosion mechanism. Traditional electrochemical techniques which are based on the Butler-Volmer equation such as the Tafel polarization technique, the linear polarization technique and the AC impedance spectroscopy, in principle, are applicable only to the measurement of the electrochemical kinetics of a uniform electrode surface, for instance, to the measurement of rates of uniform corrosion.

The fundamental limitation associated with conventional electrochemical measurement has not been overcome in despite of extensive research in this area over the past several decades. The scanning reference electrode technique and the scanning vibrating electrode technique have been used to estimate and to map current flows in the electrolyte phase, however these techniques only measure the currents in solution and not at the surface of the metal and thus the scanning results from these techniques do not delineate clearly the areas of cathodes and anodes, see H. S. Isaacs et al., "Mapping Currents at the Corroding Surface/Solution Interface", Proceedings of Research Topic Symposium, Corrosion 97, NACE, 1997, p. 65. Electrochemical impedance spectroscopy has been proposed to monitor localized corrosion, see F. Mansfeld et al., "Monitoring of Localized Corrosion with Electrochemical Impedance Spectroscopy", Corrosion 92, NACE, 1992, paper 229, however this techniques still use a conventional one piece electrode and thus it may suffer similar limitations as other conventional electrochemical methods in studying localized corrosion. Electrochemical noise analysis has also been proposed to monitor localized corrosion, see K. Haldky, "Corrosion Monitoring", U.S. Pat. No. 4,575,678 issued Mar. 11, 1986 and D. A. Eden et al., "Corrosion Monitoring", U.S. Pat. No. 5,139,627 issued Aug. 18, 1992, however this application is under development and remains controversial, see F. Mansfeld et al., "Comments", Journal of the Electrochemical Society, vol. 141, 1994, p1403. A corrosion sensor array was used to instantaneously monitor corrosion and environmental, see R. S. Glass et al., "Method for Monitoring Environmental and Corrosion", U.S. Pat. No. 5,437,773 issued Aug. 1, 1995, however that sensor appears only carrying conventional electrochemical measurements at selected isolated locations.

The present invention provides an electrochemical measurement method utilizing a unique integrated multi-sensor electrode system, namely the wire beam electrode, for measuring localized corrosion and other heterogeneous electrochemical processes. This method overcomes some major limitations associated with conventional electrochemical measurement techniques and it can be used to measure local electrochemical parameters which are important for controlling and optimizing industrial electrochemical processes. This method provides a means which is capable of detecting catastrophic localized corrosion and which is capable of monitoring heterogeneous industrial electrochemical processes such as cathodic and anodic protection of metals, electroplating, electrotyping, electrometallurgy, electrowinning and electromachining.

BRIEF SUMMARY OF THE INVENTION

It is an object of the present invention to provide a method of measuring, monitoring and studying localized corrosion and other heterogeneous industrial electrochemical processes such as cathodic and anodic protection of metals, electroplating, electrotyping, electrometallurgy, electrowinning and electromachining.

It is a further object of the present invention to provide an integrated multi-sensor electrode, namely the wire beam electrode, to simulate a conventional one-piece metal electrode surface in electrochemical behavior and to measure electrochemical parameters at local areas of the wire beam electrode surface.

A further object of the present invention is to provide an electrochemical measurement apparatus incorporating, a wire beam electrode which is exposed to a corrosive environment, a zero resistance ammeter which is inserted between each selected wire terminal of a wire beam electrode and all other coupled wire terminals to measure the coupling current flowing into or out the selected wire, a high impedance voltmeter which is used to measure the electrochemical potential of each temporarily uncoupled wire versus a reference electrode, a polarization resistance measuring apparatus which is used to measure the polarization resistance of each temporarily uncoupled wire.

Another object of the present invention is to provide a method of determining the kinetics of heterogeneous electrochemical processes using equations provided by the present invention.

Other objectives and advantages of the present invention will become apparent from the following detailed description and accompanying drawings. In general, the present invention is an electrochemical measurement method using a wire beam electrode which can be embedded in various industrial structures or electrochemical cells to obtain information on corrosion failure and on various forms of heterogeneous electrochemical processes. This information is useful for the purposes of preventing localized corrosion and for optimizing industrial electrochemical processes. Three system applications are disclosed to illustrate the present invention and related apparatus.

BRIEF DESCRIPTION OF THE SEVERAL VIEWS OF THE DRAWINGS

The accompanying drawings, which are incorporated into and form a part of the disclosure, illustrate an embodiment of the present invention and, together with the description, serve to explain the principles of the present invention.

FIGS. 2A and 2B illustrate a wire beam electrode with the configuration of a tube.

DETAILED DESCRIPTION OF THE INVENTION

The invention is an electrochemical measurement method utilizing an integrated multi-sensor electrode system, namely the wire beam electrode, for measuring localized corrosion and other heterogeneous electrochemical processes for the purposes of preventing localized corrosion and for optimizing industrial electrochemical processes. The wire beam electrode is utilized to simulate a conventional one-piece electrode surface in electrochemical behavior and to measure local electrochemical parameters at selected areas of the electrode surface. These local electrochemical parameters are utilized to characterize the thermodynamic and kinetic properties of localized corrosion and other heterogeneous electrochemical processes occurring on the wire beam electrode surface, for instance, to determine the rates of localized corrosion. This method overcomes major limitations associated with conventional electrochemical techniques in measuring localized corrosion and other heterogeneous electrochemical processes. This method can be utilized in corrosion prevention industry to measure and monitor various forms of general and localized corrosion. This method can also be utilized in electrochemical industry to control and optimize various heterogeneous electrochemical processes such as cathodic and anodic protection of metals, electroplating, electrotyping, electrometallurgy, electrowinning and electromachining.

Figure 1A:
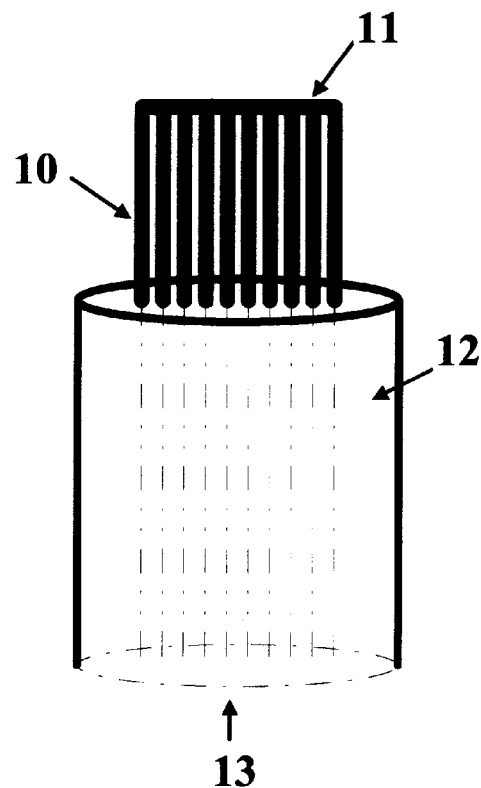
FIGS. 1A and 1B illustrate the conceptual design of the wire beam electrode.
Figure 1B:
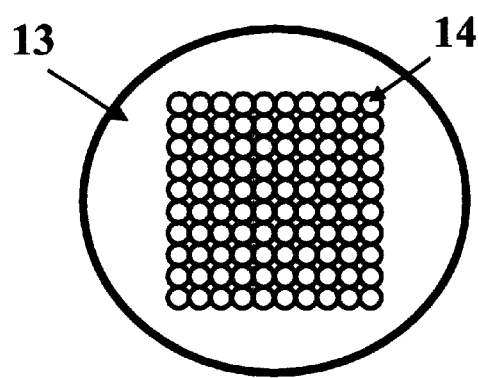
Figure 3:
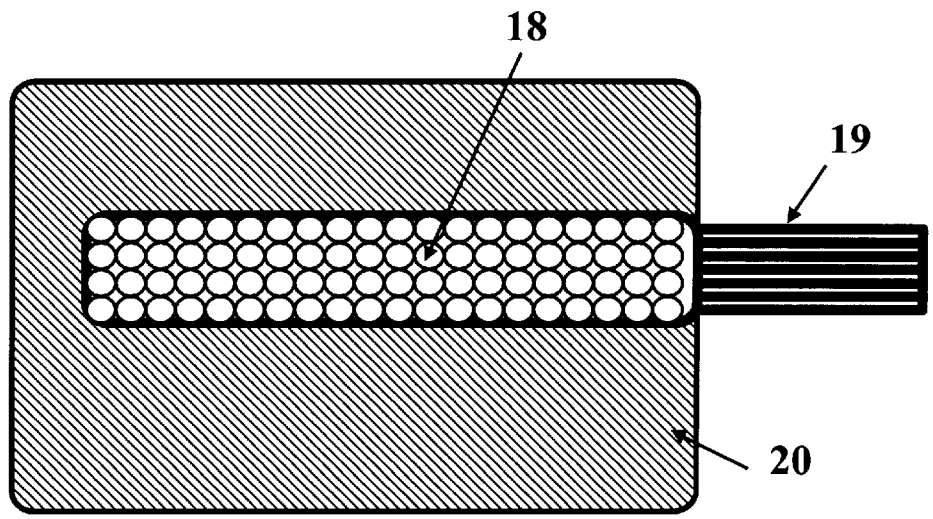
FIG. 3 illustrates a wire beam electrode with the configuration of a rod.

FIG. 1 illustrates a conceptual design of the wire beam electrode. The wire beam electrode is an integrated multi-sensor system which is usually fabricated from a bundle of electrically insulated drawn metal wires indicated at 10 with the terminals of the wire bundle connected together 11. The wire bundle is embedded in insulating material 12 such as epoxy, ceramics and rubber. The working surface of the wire beam electrode 13 contains an integrated addressable multi-sensor array 14. This multi-sensor array 14 can also be prepared by techniques such as machining, casting, laser cutting, electric arc cutting, electrodeposition or vapor deposition. The multi-sensor array 14 is usually made from identical metal, it can also made from dissimilar, galvanized, heat-treated or stressed metallic materials in order to simulate the non-uniform metallurgical composition and properties of a single piece of metal. The configuration of a wire beam electrode can be changed to meet various practical requirements. For instance, a tube-shape wire beam electrode 15 with the terminals of the wire bundle connected together 16 can be utilized to simulate and study localized corrosion in a pipeline 17, a rod-shape wire beam electrode 18 with the terminals of the wire bundle connected together 19 can be utilized to study corrosion of metal embedded in a concrete structure 20. The shape of the working surface of the wire beam electrode would simulate the surface shape of a work-piece under study. The shape and the area of the cross section of each wire used in a wire beam electrode depend upon the conditions and objectives of an electrochemical measurement. For instance, if a wire beam electrode is used to study pitting corrosion, the surface area of the cross section of each wire would be larger than the size of pits which are normally observed on large area electrode or on coupon surfaces at certain stage of pitting propagation. The larger the number of wires the better providing it is technically practical. The spacing between neighboring wires is variable although a small space is preferred to best simulate a one piece large area electrode. However, if the resistance of the electrolyte is small, a larger space between neighboring wires is usable for the wire beam electrode surface to simulate a large area electrode with an acceptable accuracy. In general, the dimensional and geometric designs for the wire beam electrode are dependent upon the size and shape of an industrial structure in an exact application. A large insulation resistance between wires is essential.

The present invention of an electrochemical measurement method utilizing a wire beam electrode is based on three scientific findings and facts. The first fact is that it has been found experimentally that the working surface of a wire beam electrode can effectively simulate uniform and localized corrosion and other heterogeneous electrochemical processes occurring on a one piece large area electrode surface. Similar corrosion patterns were observed over wire beam electrode and large area electrode surfaces when both electrodes were exposed to identical corrosion environment and this phenomenon has been explained theoretically, see Tan, Y. J. 'Monitoring localized corrosion processes and estimating localized corrosion rates using a wire beam electrode', Corrosion-NACE, vol.54, no.5, 1998, p403–413.

Indeed, in the case of uniform electrochemical processes, there is no difference in macro and micro scales between localized areas of a large electrode surface and so a large area electrode behaves in a very similar way to the parallel connection of many small individual mini-electrodes. The only difference between a large area electrode and a wire beam electrode (all the wire terminals are connected together) is that the actual working surface area of the wire beam electrode is larger because of the presence of an insulating layer between wires. This difference may affect the uniform electrochemical process to some extent if the electrochemical process is controlled by diffusion, since the larger surface area of the wire beam electrode may have some influence on the radial diffusion process. However, in most cases this influence can be ignored or be reduced through data treatment. In the case of heterogeneous electrochemical processes, electrons can move freely from anodes to cathodes through connected wire terminals of a wire beam electrode, in a similar way to that in a large area electrode. In this case, a possible difference between a wire beam electrode and a large area electrode comes from the influence of the insulating layer on the movement of ions between the localized anodes and cathodes, since the insulating layer increases the distance of ion movement in electrolyte solution. However, if the solution resistance is not too large and the insulating layer is not too thick, this influence can be ignored or be reduced during data analysis. Although a wire beam electrode will not behave exactly the same as a one-piece electrode, it can effectively simulate corrosion and other electrochemical processes occurring in a one-piece electrode with an acceptable accuracy.

Figure 4A:
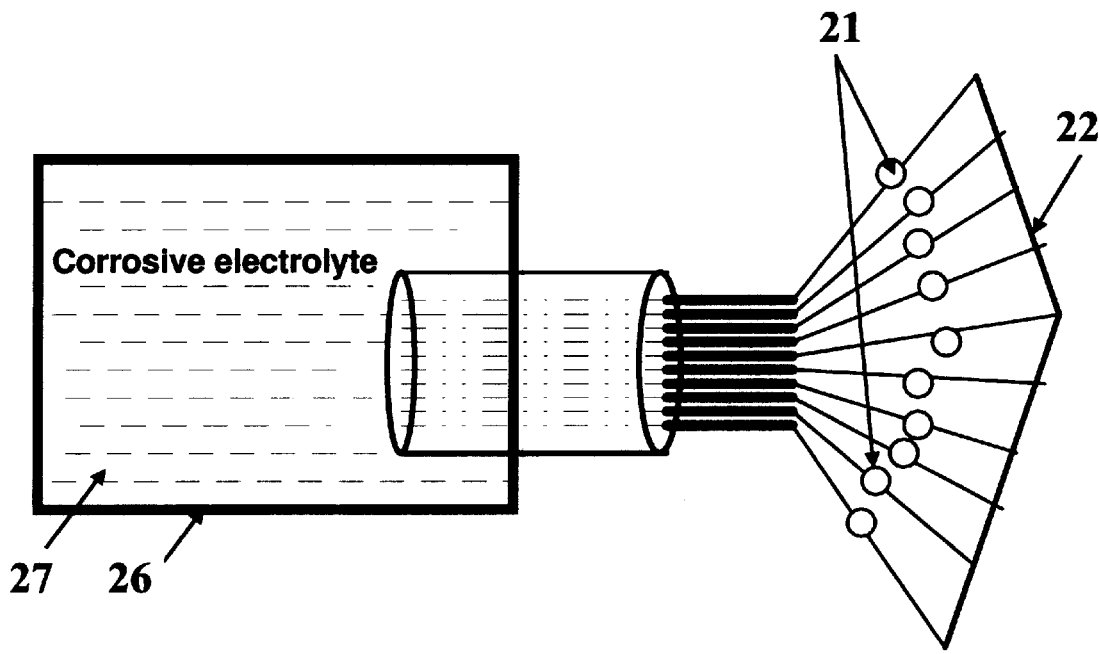
FIGS. 4A and 4B illustrate galvanic current measurement of a wire beam electrode system.
Figure 4B:
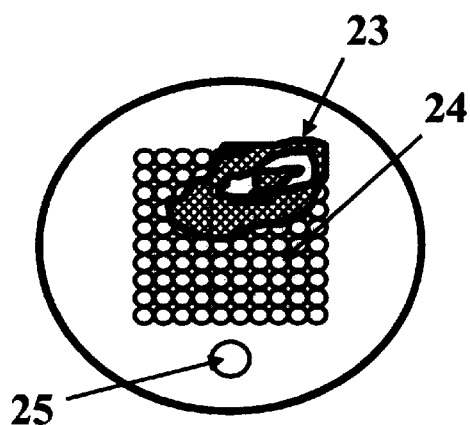
Figure 5:
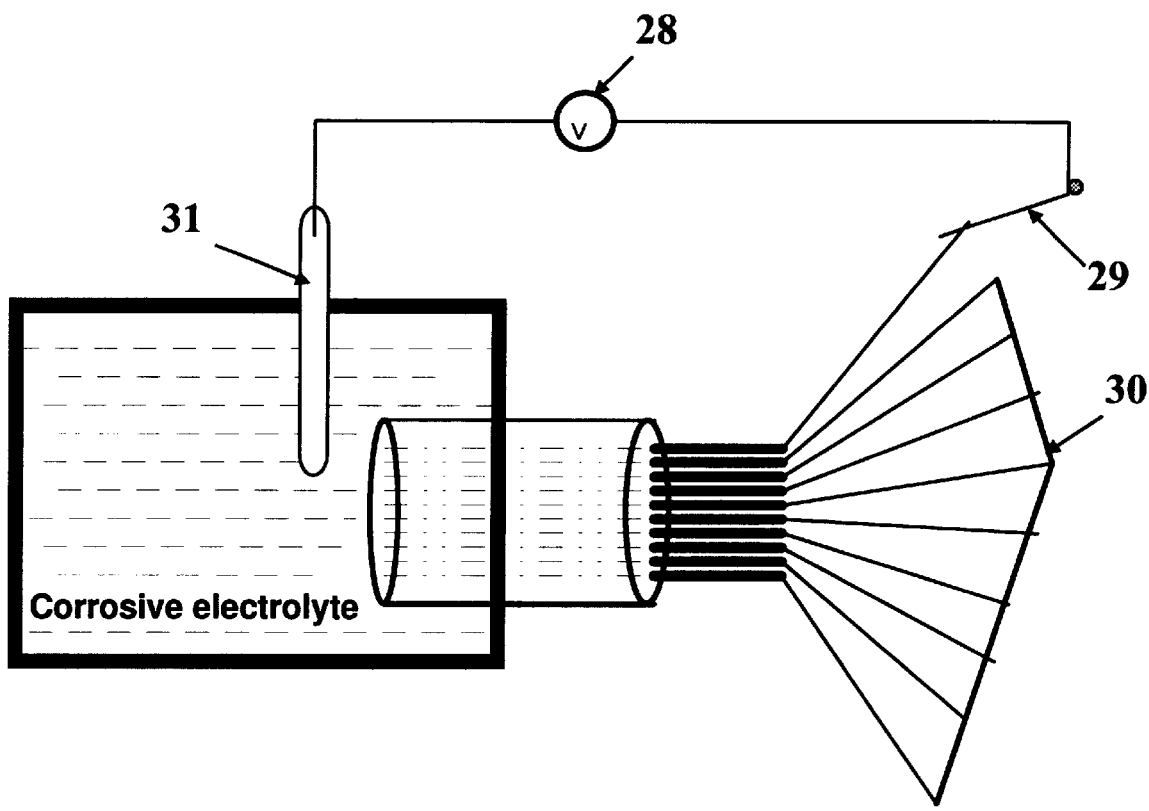
FIG. 5 illustrates electrochemical potential measurement of a wire beam electrode system.
Figure 6:
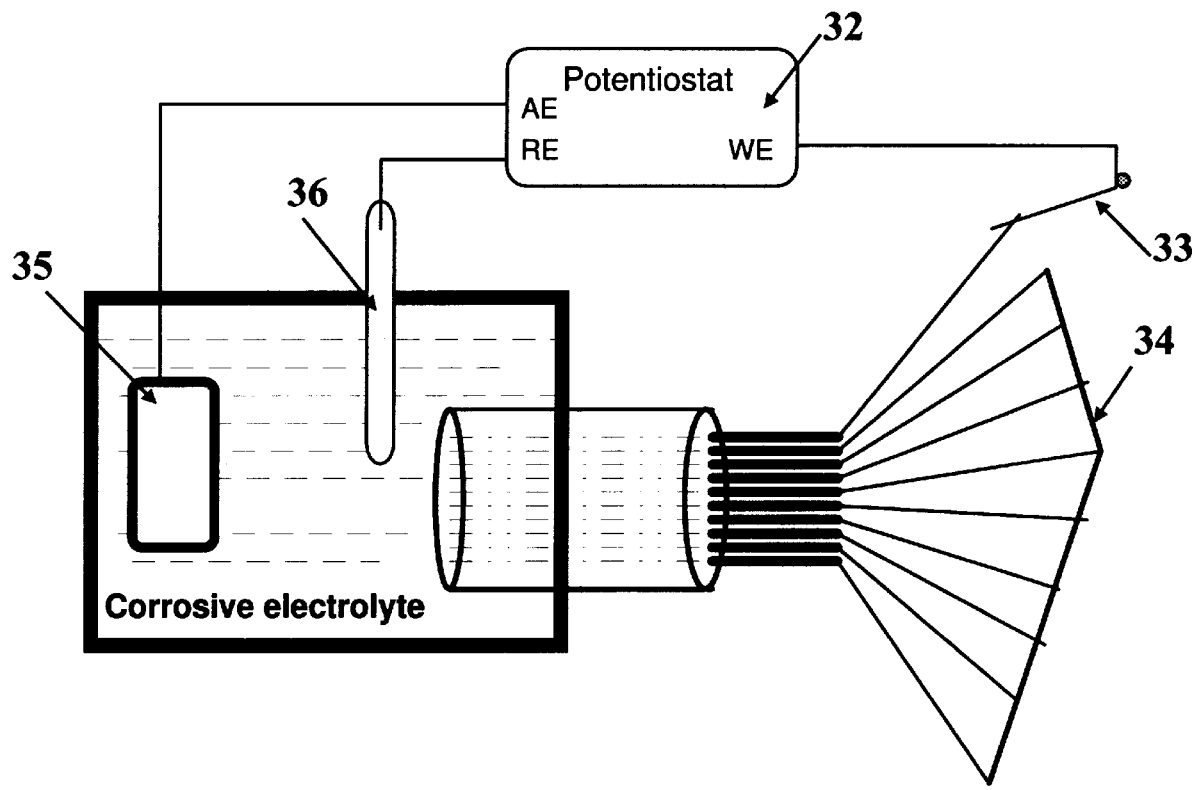
FIG. 6 illustrates electrochemical polarization measurement of a wire beam electrode system exposed to a corrosive electrolyte.

The second fact is that a wire beam electrode constitutes an integrated multi-working electrode system with each wire acting as an addressable electrochemical sensor to measure electrochemical parameters at local areas of the electrode surface. Electrons travel into or out of each wire depending on whether the wire is an anode or a cathode in the whole integrated electrochemical system. In this system, electrical current traveling through each wire terminal is measurable because zero resistance ammeters 21 can be inserted into connected wire terminals 22, as illustrated in FIG. 4. Thus galvanic currents flowing between anodic areas 23 and cathodic areas 24 on the working surface of the wire beam electrode system exposed to an electrochemical corrosion cell 26 containing electrolyte 27 can be measured. Electrochemical corrosion potential over local areas can also be measured by employing a high impedance voltmeter 28 and a reference electrode 31, as shown in FIG. 5. A selected wire in the wire beam electrode can be temporarily disconnected from the wire terminals 30 and be connected to a voltmeter 28 and a reference electrode 31 by using a switch 29. Electrochemical polarization measurement over local areas can also be performed by employing a potentiostat 32, an auxiliary electrode 35 and a reference electrode 36, as shown in FIG. 6. A selected wire in the wire beam electrode can be temporarily disconnected from the wire terminals 34 and connect to the a potentiostat 32 using a switch 33, for polarization measurement (see for examples, A. J. Bard and L. R. Faulkner, Electrochemical Methods Fundamentals and Applications, John Wiley and Sons, New York, 1980; M. G. Fontana and N. D. Greene, Corrosion Engineering, McGraw-Hill, San Francisco, 1978). In this way, heterogeneous electrochemical parameters including electrochemical potential distribution, galvanic current and polarization resistance and their distribution over the wire beam electrode surface can be measured and mapped. The specific technique used for any particular measurement will be understood by those skilled in the art.

The third fact is that the surface area of each wire in a wire beam electrode is much smaller than the whole working electrode area of a wire beam electrode, thus electrochemical processes on each corroding wire surface can be assumed to be uniform even if the whole electrode surface is electrochemically heterogeneous, an approach which is an analogy to calculus principles. This assumption allows electrochemical techniques and theories describing uniform electrochemical processes to be applied to each wire in an integrated wire beam electrode, i.e. traditional electrochemical theories and techniques are extended to study localized corrosion and other heterogeneous electrochemical processes. Based on this assumption and the traditional Butler-Volmer equation, three equations have been deduced by the inventor, see Y. J. Tan, 'Monitoring localized corrosion processes and estimating localized corrosion rates using a wire beam electrode', Corrosion-NACE, vol.54, no.5, 1998, p403–413, to calculate the electrochemical kinetics, such as localized corrosion rate, of each individual wire:

$$I_{ka} = I_k \exp[2.3(E_{sys} - E_k)/b_{ak}] \quad (1)$$

An alternative approach is as follows, $$I_{ka} = I_{gk} \bigg/ \left\{ 1 - \exp\left[-\left(\frac{2.3}{b_{ak}} + \frac{2.3}{b_{ck}}\right)(E_{sys} - E_k)\right] \right\} \quad (2)$$

Another alternative approach is as follows, $$I_{ka} = I_{gk} \quad (3)$$

In equations 1–3, $I_{ka}$ is total electrochemical anodic reaction current over the surface of a selected wire 'k' in the wire beam electrode. $I_{ka}$ is directly proportional to metal dissolution rate such as corrosion rate and can be correlated with traditional techniques such as the optical measurement of pitting corrosion depth. $E_k$ and $I_k$ are the open circuit electrochemical potential and open circuit electrochemical corrosion current of the wire 'k'. $E_k$ can be easily measured when the wire 'k' is temporarily uncoupled from the multi-piece electrode system using a voltmeter 28 via a reference electrode 31 in FIG. 5. $I_k$ can also be easily measured using traditional electrochemical techniques such as linear polarization measurements when the wire 'k' is temporarily uncoupled from the multi-piece electrode system, see Y. J. Tan, 'Monitoring localized corrosion processes and estimating localized corrosion rates using a wire beam electrode', Corrosion-NACE, vol.54, no.5, 1998, p403–413. $E_{sys}$ is the overall corrosion potential of the whole wire beam electrode system which can be easily measured using a voltmeter 28 via a reference electrode 31 when all wires in the wire beam electrode system are coupled together. $I_{gk}$ is the galvanic current flowing into or out the wire 'k' which can be measured by inserting an ammeter 21 into the coupled wire beam electrode system (FIG. 4). The Tafel slopes, $b_{ak}$ and $b_{ck}$, can be estimated by performing a polarization measurement on the wire 'k' using a potentiostat 32, an auxiliary electrode 35 and a reference electrode 36, as shown in FIG. 6, see Y. J. Tan, 'Monitoring localized corrosion processes and estimating localized corrosion rates using a wire beam electrode', Corrosion-NACE, vol.54, no.5, 1998, p403–413. The specific technique used for any particular measurement will be understood by those skilled in the art.

The choice of equation 1, 2 or 3 depends upon specific applications. Equation 1 can be applied to all cases as soon as the open circuit electrochemical corrosion current $I_k$ can be measured accurately. Equation 2 can be applied if the difference between $E_{sys}$ and $E_k$ is relatively large. Equation 2 is often more convenient than equation 1 since $I_{gk}$ can be measured more easily than $I_k$. Equation 3 is the simplified form of equation 2 under the condition that the difference between $E_{sys}$ and $E_k$ is very large (usually larger than 100 mV). Equation 3 simply takes the galvanic currents as an estimation of heterogeneous electrochemical kinetics and thus is the most convenient.

Using equation 1, 2 or 3 to each wire in the wire beam electrode, localized electrochemical corrosion currents over all locations of the wire beam electrode surface can be determined and a corrosion rate distribution map showing electrochemical kinetics over the wire beam electrode surface can be produced.

The concept of the wire beam electrode was initially developed by the inventor to detect defects in organic coatings, see Tan, Y. J. 'The effect of inhomogeneity in organic coatings on electrochemical measurements using a wire beam electrode, part 1', *Progress in Organic Coatings*, vol.19, p89–94 (1991). That work is completely different from the present invention since that work only involved the measurements of coating resistances over a coating film in order to detect defects and their distribution over an organic coating film. That work did not involve the measurement of the electrochemical processes which occur on the working surface of the wire beam electrode. For the same reason, later works which similarly applied the wire beam electrode to detect coating defects and their distribution are also different from the present invention, see Y. J. Tan and S. T. Yu, 'The effect of inhomogeneity in organic coatings on electrochemical measurements using a wire beam electrode, part 2', *Progress in Organic Coatings*, 19, p257–263 (1991); Y. J. Tan and S. T. Yu, 'Study and evaluation of organic coatings by use of a wire beam electrode', Proc. 7th Asian and Pacific Corrosion Control Conference, Beijing, p671 (1991); Y. J. Tan and S. T. Yu, 'Study and evaluation of organic coatings by use of a wire beam electrode', *Materials Protection* (China, in English and in Chinese), vol.25, no.6, p4–13 (1992); C. L. Wu, X. J. Zhou and Y. J. Tan, 'A study on the inhomogeneity of organic coatings', *Progress in Organic Coatings*, vol.25, p379–389 (1995); C. L. Wu, Q. D. Zhong and J. C. Jin, 'Study on Electrochemical inhomogeneity on oil-pained metal', *Corrosion Science and Protection Technology* (China), vol.8, no.3, p256 (1996); G. F. Huang, C. L. Wu and J. C. Jin, 'Study on protective behaviour of rust preventing oil by wire beam electrode', *Materials Protection* (China), vol.29, no.4, p9 (1996). The wire beam electrode was also firstly applied by the inventor in 1994 to study crevice corrosion using a simple experimental device, see Y. J. Tan, 'A new method for crevice corrosion studies and its use in the investigation of oil-stain', Corrosion-NACE, no.4, vol.50, p266–269 (1994). That work only used a wire beam electrode whose wire terminals were all permanently separated and thus that work failed to simulate a large area electrode surface and did not measure electrochemical kinetics, see Y. J. Tan, 'A new method for crevice corrosion studies and its use in the investigation of oil-stain', Corrosion-NACE, no.4, vol.50, p266–269 (1994). In general, all these previous developments are different from the present invention and are less valuable in studying heterogeneous electrochemical processes.

Some component parts of the present invention have been published under the name of the inventor in November 1997, see Y. J. Tan, 'Wire beam electrode: a new tool for localized corrosion studies', Proc. Australasia Corrosion Association Conference Corrosion & Prevention 97, Brisbane, Australia, paper no.52 (1997) and in May 1998, see Y. J. Tan, 'Monitoring localized corrosion processes and estimating localized corrosion rates using a wire beam electrode', Corrosion-NACE, vol.54, no.5, p403–413 (1998).

This invention will be more fully understood by reference to the following examples, which are intended to be representative applications of the invention, but not limiting thereof. The invention is limited only by the claims appended hereto.

EXAMPLE 1

Measuring Localized Corrosion

When localized corrosion occurs on the working surface of a wire beam electrode, with all wire terminals connected together, some of the electrode areas become anodes which are under corrosion, and the other electrode areas become cathodes which are under cathodic protection. During the processes, electrons continuously travel from the anode areas to the cathode areas through the connected wire terminals while ions travel between anode and cathode areas through the electrolyte. This electrical current is called galvanic current which is measurable using an experimental arrangement as shown in FIG. 4, where current between local anodes and cathodes is measured by inserting zero resistance ammeters 21 into the connected terminals of wires 22. Alternatively, a single zero resistance ammeter can be used to achieve the same objective by using a pre-programmed automatic switch which connects, in sequence, the ammeter to each terminal of the wire. Corrosion potential of each wire can be measured using an experimental arrangement as shown in FIG. 5, where a high impedance voltmeter 28 and a reference electrode 31 are used to measure the corrosion potential of each selected wire. The reference electrode can be a conventional reference electrode such as Ag/AgCl electrode or any electrode which has relatively stable potential. One or more extra wires can be added to the wire beam electrode system to act as a 'built-in' reference electrode 25. The voltmeter 28 is connected in sequence with each wire terminal and the corrosion potentials vs. a reference electrode 31 are recorded and a corrosion potential distribution map can be produced.

Figure 7A:
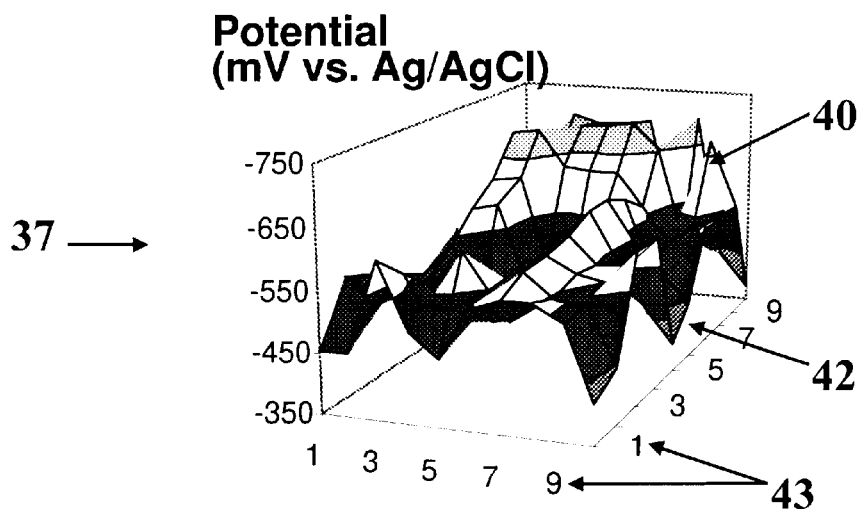
FIGS. 7A, 7B and 7C illustrate the distributions of galvanic current and corrosion potential measured from a wire beam electrode system exposed to a water-line corrosion environment.
Figure 7B:
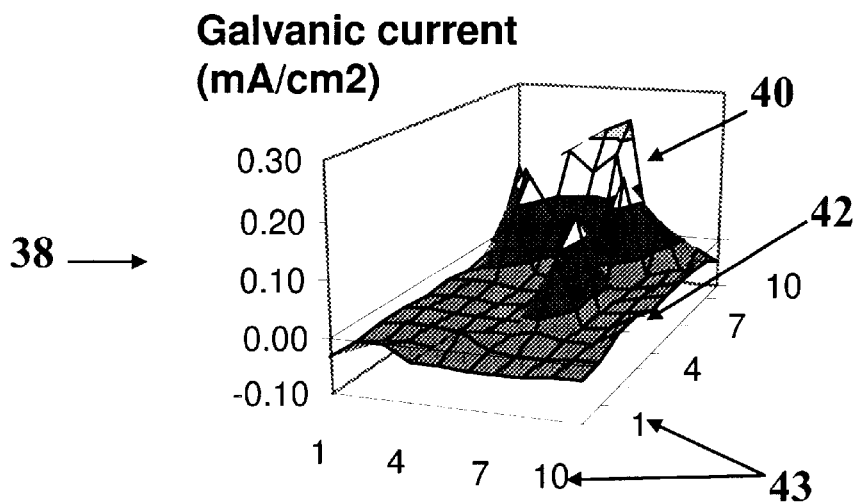
Figure 7C:
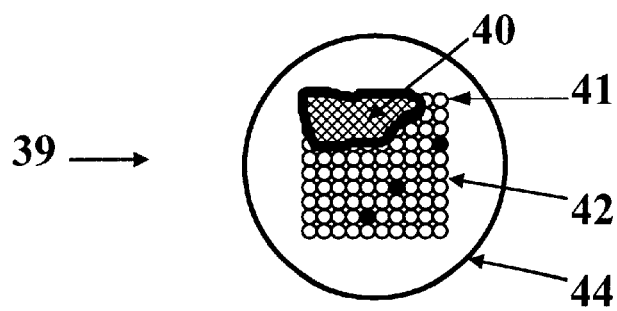

Water-line corrosion is a well-known localized corrosion phenomenon. When a steel plate is partly immersed in a unstirred solution containing a corrosive salt (e.g. sodium chloride) with insufficient amount of inhibitor (e.g. sodium carbonate), intense localized corrosion occurs along the water line areas on the plate. FIG. 7 shows potential (FIG. 7A) and galvanic current (FIG. 7B) distributions and visual observations (FIG. 7C) over a wire beam electrode working surface during partial exposure to 0.017 M NaCl+0.008 M $Na_2CO_3$ solution. During the experiment, initially only a few isolated anodic sites appeared among a large number of cathodic sites. After 5 days' exposure, as clearly shown in the potential 37, galvanic currents 38 and visual observation 39 diagrams, corrosion expanded and some of the anodic sites merged together to form a larger localized corrosion zone 40 along the water-line level area 41. No visible corrosion occurred at cathodic areas 42 where are indicated by higher corrosion potentials. There is very good agreement between visual observation 39 and the corrosion potential 37 and galvanic current 38 distributions. Wire serial numbers 43 address the wire beam electrode surface 44. This experiment illustrates localized corrosion processes due to a large cathodic zone and small anodic zones. This experiment clearly proves that galvanic current and corrosion potential distribution maps can be used to monitor the occurrence, processes and patterns of localized corrosion. It was also found during a 6 days' exposure test, that similar visual changes were observed over the working surface of the wire beam electrode and over the surface of a large area mild steel plate immersed in the same electrolyte, see Y. J. Tan, 'Monitoring localized corrosion processes and estimating localized corrosion rates using a wire beam electrode', Corrosion-NACE, vol.54, no.5, 1998, p403–413. This localized corrosion system exhibited large potential differences between anodic and cathodic zones, equation 3 can thus be used to calculate instantaneous localized corrosion currents and their distribution over the electrode surface. Table I is a comparison of localized corrosion rates calculated using equation 3 and traditional solution analysis method. This new method shows a very good correlation with traditional solution analysis method.

TABLE I

A comparison of localized corrosion rates obtained using the wire beam electrode method and solution analysis

| Conditions | Corrosion Pattern | Corrosion Rate (wire beam electrode method) | Corrosion Rate (Solution Analysis) |
| --- | --- | --- | --- |
| Partial exposure to 0.017M NaCl + 0.008M $Na_2CO_3$ solution for about 6 days | Water-line corrosion and localized attack | 1.39 mm/y. | 1.32 mm/y |
| Partial exposure to 0.017M NaCl solution for about 5 days | Localized corrosion | 0.34 mm/y | 0.37 mm/y |
| Total exposure to 0.017M NaCl solution for about 20 hours | Localized corrosion | 0.13 mm/y | 0.19 mm/y |

The determination of corrosion rates enables us to predict localized corrosion trend, and to evaluate localized corrosion inhibitors and prevention methods. The present invention provides a new and unique means of assessing corrosion of various forms in industrial structures such as bridges, ships, aircrafts, vehicles, oil and gas wells, etc.

EXAMPLE 2

Measuring Cathodic and Anodic Protection

Figure 8:
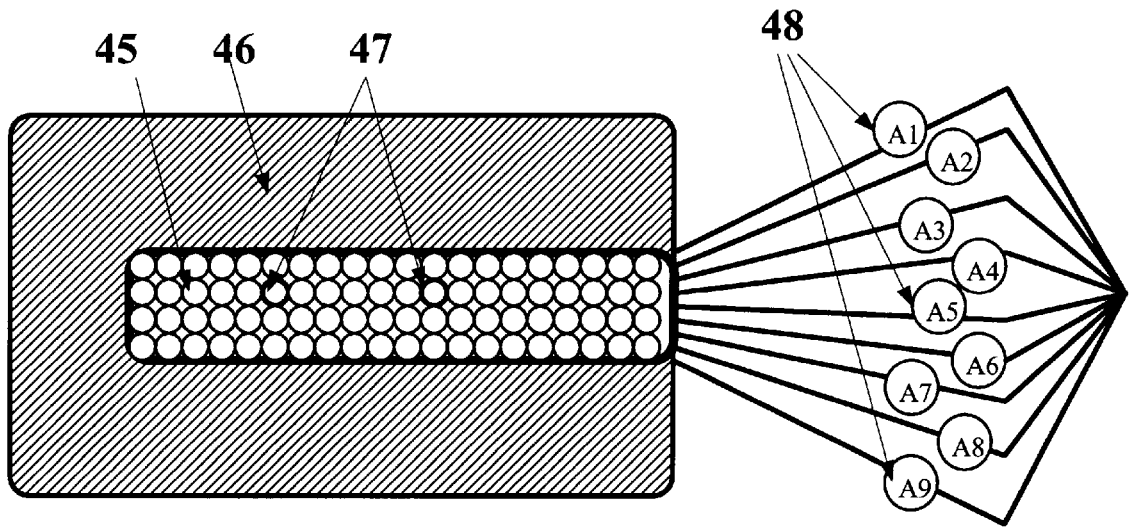
FIG. 8 illustrates the measurement of cathodic protection current distribution over a wire beam electrode surface exposed to a concrete structure with sacrificial anodes present.

A very important design requirement for cathodic and anodic protection of metal structures is that the necessary range of protection current is achieved at all areas of the structure. It is well known that protection current is normally distributed non-uniformly on a metal structure surface since protection current distribution is exclusively related to the geometry of the metal structure and corrosive environment. Knowledge of protection current distribution is important since non-uniform protection current distribution could cause over-protection or under-protection of some sections of the structure, especially when the structure has a complex shape. Protection current or potential distribution is normally modeled and calculated mathematically. However, mathematical modeling and calculation are often difficult for complex shapes. The present invention provides a solution to the direct measurement of protection currents and their distribution. FIG. 8 shows measurement of protection current distribution using a rod-shape wire beam electrode system 45, which simulates the installation of sacrificial anodes in a reinforced concrete structure 46. Two wires of the wire beam electrode 47 are made from metal which provides sacrificial anodic protection current to prevent other wires from corrosion. However, anodic protection current is non-uniformly distributed. More electrons flow to the wires which are closer to the anodes while fewer electrons flow to the wires which are far from the anodes. This non-uniform current distribution can be measured using ammeters 48. Alternatively, a single zero resistance ammeter can be used to achieve the same objective by using a computer controlled switch which automatically connects, in sequence, the ammeter to each selected terminal of the wire.

Figure 9:
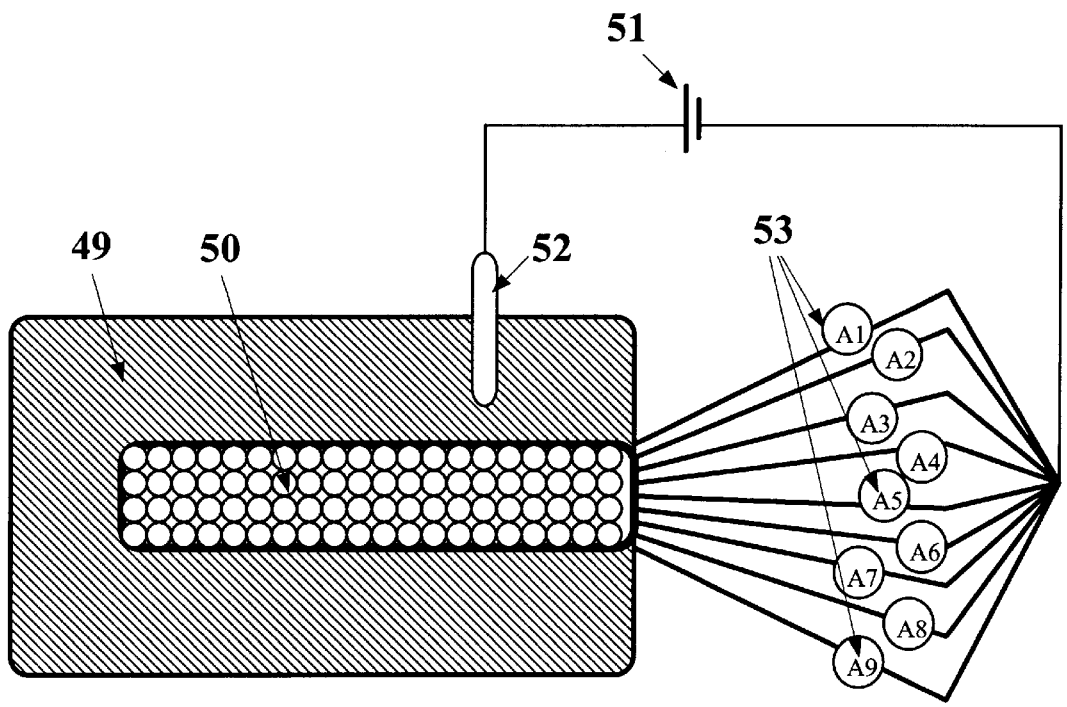
FIG. 9 illustrates the measurement of cathodic protection current distribution over a wire beam electrode surface which is under impressed current cathodic protection.

In the case of impressed current protection of a reinforced concrete structure 49, as shown in FIG. 9, protection current distribution can be measured using a rod-shape wire beam electrode system 50. The non-uniform distribution of protection current, supplied by an external protection current source 51 and an anode 52, can be measured using ammeters 53. Alternatively, a single zero resistance ammeter can be used to achieve the same objective by using a switch which automatically connects, in sequence, the ammeter to each terminal of the wire.

In this application, the space between wires in the wire beam electrode can be varied according to the resistance of the corrosive media and the requirement for measurement accuracy. If the resistance of the corrosion media is not too high, large space between wires can still ensure that the wire beam electrode surface effectively simulates a real metal structure with an acceptable accuracy. For a given industrial application, several wire beam electrodes, perhaps hundreds or thousands for a large structure, would be emplaced on various selected locations of the structure.

EXAMPLE 3

Measuring Electroplating, Electro-machining, Electrotyping and Electrowinning

In the cases of electroplating, electro-machining, electrotyping and electrowinning processes, impressed current (anodic or cathodic) distribution is exclusively related to the geometry of a work-piece. This current distribution is a major concern during these processes, for example, electroplating requires a reasonably uniform current distribution if a uniform metal deposition is required. Although this distribution could be calculated mathematically, this is normally very difficult if the work-piece has a complex shape.

Figure 10:
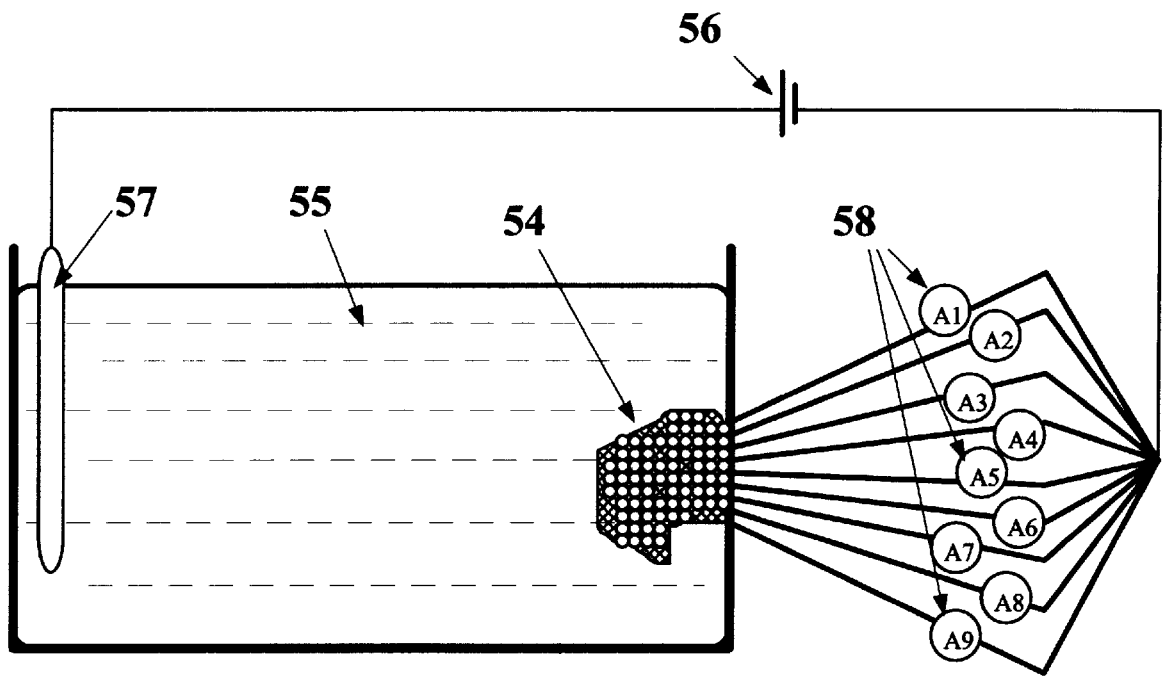
FIG. 10 illustrates the measurement of electroplating current distribution over a wire beam electrode surface.

The present invention provides a method of measuring this current distribution. FIG. 10 shows an experimental arrangement for measuring the distribution of electroplating current using a complexly shaped wire beam electrode 54, which simulates a complexly shaped work-piece surface under study. When the wire beam electrode is exposed to an electroplating bath 55 and electroplating current is applied by an external current source 56 and an electroplating anode 57, electroplating current distribution over the wire beam electrode 54 can be measured using ammeters 58. Alternatively, a single zero resistance ammeter can be used to achieve the same objective by using a switch which automatically connects, in sequence, the ammeter to each terminal of the wire. For a given industrial application, more than one wire beam electrode would be emplaced on various selected locations of an electrochemical bath.

I claim:

1. A method for measuring localized corrosion and other heterogeneous electrochemical processes comprising the steps of:

forming an integrated multi-sensor wire beam electrode system whose working surface simulates a conventional one piece metal electrode surface in electrochemical behavior;

exposing the working surface of the wire beam electrode to an electrolyte as a conventional one-piece electrode surface to allow localized corrosion or other heterogeneous electrochemical processes to occur;

measuring local electrochemical parameters from local areas of the wire beam electrode surface by means of wires located at these local areas using read-out means;

calculating local electrochemical kinetics of localized corrosion and other heterogeneous processes by means of kinetic equations derived based on the wire beam electrode concept.

2. The method of claim 1, wherein the wire beam electrode is fabricated from an array of at least three identical or dissimilar metallic sensors, whose terminals are all coupled together to form an integrated working surface; whose working surface simulates the shape, the metallurgical composition and electrochemical behavior of a conventional one-piece electrode surface.

3. The method of claim 1, wherein the step of measuring local electrochemical parameters is carried out by operatively connecting each of the individual wire sensors in a wire beam electrode to an electronic/computational system, such that each individual wire sensor is measured for the coupling current flowing into or out of the selected wire sensor, for the electrochemical potential of the selected wire sensor versus the reference electrode, for the polarization resistance of the selected wire sensor, and for the Tafel constants of the selected wire sensor.

4. The method of claim 1, wherein the step of calculating local electrochemical kinetics was carried out by fitting local electrochemical parameters to equation 1:

$$I_{ka} = I_k \exp[2.3(E_{sys} - E_k)/b_{ak}] \quad (1)$$

or by fitting local electrochemical parameters to equation 2:

$$I_{ka} = I_{gk} \Big/ \left\{ 1 - \exp\left[-\left(\frac{2.3}{b_{ak}} + \frac{2.3}{b_{ck}}\right)(E_{sys} - E_k)\right] \right\} \quad (2)$$

or by fitting local electrochemical parameters to equation 3:

$$I_{ka} = I_{gk} \quad (3)$$

where $I_{ka}$ is total electrochemical anodic reaction current which describes overall electrochemical corrosion reaction kinetics over the surface of a selected wire k in the wire beam electrode; where $E_k$ and $I_k$ are the open circuit potential and open circuit electrochemical corrosion current of the wire sensor k; where $E_{sys}$ is the overall electrochemical corrosion potential of the whole wire beam electrode system; where $I_{gk}$ is the galvanic current flowing into or out the wire sensor k; where $b_{ak}$ and $b_{ck}$ are the Tafel slopes of wire sensor k.

5. An apparatus for measuring localized corrosion and other heterogeneous electrochemical processes comprising:

an integrated wire beam electrode system whose terminals are all coupled together to simulate a conventional one piece metal electrode surface in electrochemical behavior;

a zero resistance ammeter which is inserted between each selected wire terminal of a wire beam electrode and all other coupled wire terminals to measure the coupling current flowing into or out the selected wire;

a high impedance voltmeter which is used to measure the electrochemical potential of each temporarily uncoupled wire versus a reference electrode;

a polarization resistance measuring apparatus which is used to measure the polarization resistance of each temporarily uncoupled wire.

* * * * *